(12) United States Patent
Sathya et al.

(10) Patent No.: US 11,723,543 B2
(45) Date of Patent: Aug. 15, 2023

(54) NON-INVASIVE SYSTEM AND METHOD FOR MEASURING BLOOD PRESSURE VARIABILITY

(71) Applicant: CHRISTIAN MEDICAL COLLEGE, TamilNadu (IN)

(72) Inventors: Subramani Sathya, TamilNadu (IN); Jebaraj Benjamin, TamilNadu (IN)

(73) Assignee: Christian Medical College, Tamil Nadu (IN)

( * ) Notice: Subject to any disclaimer, the term of this patent is extended or adjusted under 35 U.S.C. 154(b) by 510 days.

(21) Appl. No.: 16/300,962

(22) PCT Filed: May 17, 2017

(86) PCT No.: PCT/IB2017/052899
§ 371 (c)(1),
(2) Date: Nov. 13, 2018

(87) PCT Pub. No.: WO2017/199174
PCT Pub. Date: Nov. 23, 2017

(65) Prior Publication Data
US 2019/0200879 A1 Jul. 4, 2019

(30) Foreign Application Priority Data
May 20, 2016 (IN) .............................. 201641017475

(51) Int. Cl.
*A61B 5/0205* (2006.01)
*A61B 5/00* (2006.01)
(Continued)

(52) U.S. Cl.
CPC ............ *A61B 5/0205* (2013.01); *A61B 5/021* (2013.01); *A61B 5/02416* (2013.01);
(Continued)

(58) Field of Classification Search
CPC ......... A61B 5/0205; A61B 5/08; A61B 5/021; A61B 5/022; A61B 5/02416;
(Continued)

(56) References Cited

U.S. PATENT DOCUMENTS 4,754,761 A * 7/1988 Ramsey, III ........... A61B 5/022
600/494
6,120,459 A * 9/2000 Nitzan ................ A61B 5/02125
600/485
(Continued)

FOREIGN PATENT DOCUMENTS

EP          0333332      9/1969
JP          2000083911   3/2000

OTHER PUBLICATIONS

S Omboni and G Parati and A Frattola and E Mutti and M Di Rienzo and P Castiglioni and G Mancia, "Spectral and sequence analysis of finger blood pressure variability. Comparison with analysis of intra-arterial recordings", Jul. 1993, Hypertension, vol. 22, p. 26-33 (Year: 1993).*
(Continued)

*Primary Examiner* — Daniel L Cerioni
*Assistant Examiner* — Jonathan E. Cooper
(74) *Attorney, Agent, or Firm* — Mark M. Friedman

(57) ABSTRACT

A non-invasive system and method for measuring blood pressure variability includes a cuff (20) pneumatically connected to a pump (14) to inflate the cuff to be wrapped around a limb (21) of a subject. A pressure sensor (18) is associated with the cuff for measuring cuff pressure (52). A photoplethysmogram sensor (26) attached to a fingertip in the same limb (21) of the subject and placed distal to the cuff for monitoring blood flow and recording a pulse plethysmograph signal. A control unit (12) connected to the pressure sensor (18) and the photoplethysmogram sensor (26) for simultaneously recording the cuff pressure and the
(Continued)

plethysmograph signal such that an empirical relationship is derived between the cuff pressure and an amplitude measure of the plethysmograph signal (54) to measure short-term variation in systolic and diastolic blood pressures at a frequency corresponding to respiratory cycle.

8 Claims, 9 Drawing Sheets

(51) Int. Cl.
| | |
|---|---|
| *A61B 5/113* | (2006.01) |
| *A61B 5/021* | (2006.01) |
| *A61B 5/022* | (2006.01) |
| *A61B 5/053* | (2021.01) |
| *A61B 5/08* | (2006.01) |
| *A61B 5/024* | (2006.01) |
| *A61B 5/0235* | (2006.01) |

(52) U.S. Cl.
CPC .......... *A61B 5/0816* (2013.01); *A61B 5/1135* (2013.01); *A61B 5/6824* (2013.01); *A61B 5/6826* (2013.01); *A61B 5/7278* (2013.01); *A61B 5/022* (2013.01); *A61B 5/0235* (2013.01); *A61B 5/02427* (2013.01); *A61B 5/053* (2013.01); *A61B 2562/0219* (2013.01); *A61B 2562/0261* (2013.01)

(58) Field of Classification Search
CPC . A61B 5/0235; A61B 5/0225; A61B 5/02108; A61B 5/02405; A61B 5/02141; A61B 5/02233; A61B 5/02125; A61B 5/02007; A61B 5/02208; A61B 5/02255; A61B 5/02116; A61B 5/1135; A61B 5/6824; A61B 5/7278; A61B 5/0816; A61B 5/6826; A61B 2562/0261; A61B 2562/0219; A61B 5/02427; A61B 5/053
USPC ...................................................... 600/485
See application file for complete search history.

(56) References Cited

U.S. PATENT DOCUMENTS

| | | | | |
|---|---|---|---|---|
| 7,641,614 | B2* | 1/2010 | Asada | A61B 5/6838 |
| | | | | 600/485 |
| 8,047,998 | B2 | 11/2011 | Kolluri et al. | |
| 8,602,997 | B2 | 12/2013 | Banet et al. | |
| 2007/0055163 | A1* | 3/2007 | Asada | A61B 5/6838 |
| | | | | 600/490 |
| 2007/0106163 | A1* | 5/2007 | Friedman | A61B 5/02255 |
| | | | | 600/485 |
| 2007/0239039 | A1* | 10/2007 | Yang | A61B 5/332 |
| | | | | 600/483 |
| 2008/0269619 | A1* | 10/2008 | Lindberg | A61B 5/02108 |
| | | | | 600/480 |
| 2011/0144918 | A1* | 6/2011 | Inoue | A61B 5/0225 |
| | | | | 702/179 |
| 2014/0066732 | A1 | 3/2014 | Addison et al. | |
| 2017/0196469 | A1* | 7/2017 | Han | A61B 5/0816 |
| 2018/0042501 | A1* | 2/2018 | Adi | A61B 5/0004 |
| 2018/0199893 | A1* | 7/2018 | Hübner | A61B 5/0816 |

OTHER PUBLICATIONS

D. Su, C. Miao, "Blood Pressure Variability And Organ Damage", Dec. 20, 2001, Clinical and Experimental Pharmacology and Physiology, vol. 28, Issue 9, pp. 709-715 (Year: 2001).*
S. Usman, R. Mohamad Rozi, M. B. I. Reaz and M. A. Mohd Ali, "Analysis of area under curve of PPG and its relation with HbA1c," 2012 IEEE-EMBS Conference on Biomedical Engineering and Sciences, Langkawi, 2012, pp. 260-263 (Year: 2012).*
McGrath, S; Ryan, K; Wendelken, S; Rickards, C; Convertino, V, "Pulse Oximeter Plethysmographic Waveform Changes in Awake, Spontaneously Breathing, Hypovolemic Volunteers", Feb. 2011, Anesthesia & Analgesia:—vol. 112—Issue 2—p. 368-374 (Year: 2011).*
Li Yanjun et al. "Australasian Physical and Engineering Sciences in Medicine"; Apr. 11, 2014 Medicine, Melbourne, AU; vol. 37,Nr:2,pp. 367-376; XP035317069.

* cited by examiner

NON-INVASIVE SYSTEM AND METHOD FOR MEASURING BLOOD PRESSURE VARIABILITY

TECHNICAL FIELD OF THE INVENTION

The present invention relates to a blood pressure measuring system, and more particularly relates to a non-invasive blood pressure measuring system for measuring a range of systolic and diastolic pressure and their short-term variability.

BACKGROUND OF THE INVENTION

Hypertension is a disease of world-wide significance. The criteria for diagnosis of hypertension are: systolic pressure >140 mmHg and/or diastolic pressure >90 mmHg. For Isolated Systolic Hypertension (ISH) which is the commoner type occurring in older individuals beyond 60 years of age, the criterion is: systolic pressure >140 mmHg and diastolic pressure <90 mmHg.

Blood pressure is a highly varying signal, with the systolic and diastolic pressures varying from beat to beat, at a frequency which is often a respiratory frequency. This phenomenon is termed as blood pressure variability (BPV). Given BPV, single point criteria as mentioned in the previous paragraph are inadequate to detect hypertension. Even ruling out white coat hypertension in which a patient's blood pressure is elevated during the examination process due to nervousness and anxiety caused by being in a clinical setting, blood pressure variability per se can lead to spurious diagnosis of hypertension. Blood pressure variability is also gaining importance as a risk predictor for target organ damage.

Conventional approaches for estimating blood pressure is by recording the blood pressure in real time with a pressure transducer placed intra arterially for e.g., in a radial artery. Such approach provides real time data on blood pressure and is the preferred method in an intensive care setting. However, it is not feasible in a clinic or in a ward to place an arterial catheter for pressure measurement. Therefore, non-invasive methods for assessing blood pressure are preferred.

The prior art manual non-invasive blood pressure monitoring method is based on "Korotkoff" sounds. An inflatable rubber cuff is wrapped around the arm and is inflated with air to a pressure well above the systolic pressure. When cuff pressure is below the diastolic pressure, flow is pulsatile and stream-lined and does not lead to a sound when a stethoscope is placed over a section of the artery distal to the cuff. When the cuff pressure is above systolic, there is no flow at all, and therefore no sound. However, if the cuff pressure is between systolic and diastolic, flow occurs during a fraction of a cardiac cycle. The flow is not stream-lined, is turbulent and generates an auscultatory sound called the Korotkoff sound. While deflating the inflated cuff, the cuff pressure at which the Korotkoff sounds are first heard is taken as the systolic pressure and the cuff pressure at which the sounds cease is taken as the diastolic pressure. Such prior art cuff method returns one value for the systolic and diastolic pressures while the intra-arterial recording shows that these pressures vary beat to beat from a maximum to a minimum during a respiratory cycle. This method assesses systolic pressure at a particular cardiac cycle and the diastolic pressure during a cycle which is a few beats away.

One problem associated with the Korotkoff method is the assumption that there is no change in either systolic or diastolic pressures in the cardiac cycles during the cuff deflation phase. Another problem is that the assessment of when the sounds begin and cease is subjective and the inter observer variation is high. Additionally, the speed of deflation of the cuff is subjective, because if the rate of deflation is high, then by the time the observer realizes a change in sound intensity, the cuff pressure could have dropped significantly, be it the mercury manometer that records pressure or an aneroid type manometer. Furthermore, there is no assessment in the variations of systolic, diastolic and therefore mean pressures that occur with respiration and the pulse pressure assessment can be very erroneous depending on the profile of deflation.

Another prior art approach for measurement of blood pressure is "Oscillometry". In this method, the inflatable cuff is applied like Korotkoff method and the cuff pressure is increased beyond the systolic pressure and then gradually deflated and recorded. Added to the steady drop in cuff pressure during deflation, there are oscillations in cuff pressure during the deflation process. The cuff pressure recording is then high pass filtered suitably to get the oscillations in pressure and the oscillations are amplified. The highest oscillation occurs at mean arterial pressure and identifying the cuff pressure at which the oscillation of maximum amplitude occurs is a reliable method of estimating the mean pressure.

In this method the systolic and diastolic pressures are calculated from the oscillometric data. For example, the systolic and diastolic can be taken as the cuff pressures at which the amplitudes of oscillation are and 45% of the highest oscillation amplitude, to the left and right of the highest oscillation respectively. Furthermore, all drawbacks of Korotkoff method also apply to the oscillometric method. Even if the oscillometric method estimates the systolic and diastolic similar to a carefully performed manual method, by an experienced technician, all draw backs of the manual Korotkoff method also apply to the oscillometric method.

Another prior art method is by measurement of systolic pressure with cuff deflation and detection of pulse with a pulse plethysmogram. In this method, the cuff is placed around the arm and gradually inflated. Plethysmography wave form from the finger in that limb is recorded simultaneously. The cuff pressure when the pulse pleth waveform disappears is taken as the systolic pressure. However, the inflated cuff and plethysmography detects only systolic pressures but cannot estimate diastolic pressures or mean arterial pressure.

Finapres is a non-invasive proprietary instrument which gives pressure waves in real time like the intra-arterial recording. The technique involves the plethysmograph attached to a finger which tracks volume changes in the finger due to blood flow. The inflatable cuff is also wrapped around the finger and the cuff pressure measured. The plethysmograph senses volume changes and the information from the plethysmograph is fed to an automated pump which would inflate the cuff to the minimum pressure that would prevent an increase in finger volume—(i.e., prevention of flow). This volume-clamp method is said to track arterial pressure in real time. Applanation tonometry is another method which gives blood pressure waveforms like Finapres. But these conventional devices are very expensive. In summary, there is no cost-effective non-invasive method that gives an accurate estimate of not only mean systolic and diastolic pressures, but also their beat-beat variability.

Furthermore, such conventional non-invasive methods for estimating the blood pressure provide point estimates of a highly varying phenomenon. Further, the beat-to-beat variability of the blood pressure can itself lead to spurious diagnosis of hypertension if the blood pressure is measured with the current cuff-based subjective methods. Lack of awareness of this phenomenon and lack of non-invasive tools to assess the blood pressure, taking into account its beat-to-beat variability, remain an unattended problem.

Moreover, the differences in pulse pressure that occur during such measurements is a big cause for concern, especially if one has to make treatment decisions for isolated systolic hypertension (ISH), which is the form occurring in more than 60% of people aged beyond 50 years. The current recommendation is that a pulse pressure more than 63 mmHg must be considered as ISH and must be treated in such a manner to bring down the systolic but not let the diastolic drop below 65 mmHg. Such fine tuning of treatment is impossible if the recordings of blood pressure are made with any of the non-invasive methods mentioned above.

Therefore, a need exists for an improved cost-effective non-invasive system and method for accurately measuring the systolic and diastolic blood pressure and their beat-to-beat variability, as described in greater detail herein.

SUMMARY OF THE INVENTION

The following summary is provided to facilitate an understanding of some of the innovative features unique to the disclosed embodiments and is not intended to be a full description. A full appreciation of the various aspects of the embodiments disclosed herein can be gained by taking the entire specification, claims, drawings, and abstract as a whole.

It is, therefore, one aspect of the present invention to provide an improved cost-effective non-invasive blood pressure measuring system and method that is capable of estimating a range of systolic and diastolic pressures and their short-term variability during the recording.

It is another aspect of the present invention to provide an improved blood pressure measuring system that utilizes a pneumatic cuff, respiration measurement and photoplethysmography to enable estimation of the systolic and diastolic pressures during measurement of the blood pressure variability.

It is further aspect of the present invention to provide an improved blood pressure measuring method that is capable of accurately measuring an average systolic and diastolic pressure, mean pulse pressure and also their variability.

In one aspect of the present invention, a non-invasive blood pressure variability measuring system includes a cuff pneumatically connected to a pump to inflate the cuff wrapped around a limb of a subject and a pressure sensor associated with the cuff for measuring cuff pressure. A photoplethysmogram sensor attached to a fingertip in the same limb of the subject and placed distal to the cuff for monitoring blood flow and recording a pulse plethysmograph signal. A control unit is connected to the pressure sensor and the photoplethysmogram sensor for simultaneously recording the cuff pressure and the plethysmograph signal so that an empirical relationship is derived between the cuff pressure and an amplitude measure of plethysmograph signal to measure short term variation in systolic and diastolic blood pressures at a frequency corresponding to that of respiratory cycle.

A respiration sensor is placed on a subject's chest to ensure measurement of the systolic and diastolic pressure variation for at least one respiratory cycle. The respiration sensor includes a chest distension sensor belt or a chest electrical impedance respiration sensor. The photoplethysmogram sensor includes a reflective plethysmograph sensor or a transmittive plethysmograph sensor. The cuff is inflated from a low pressure below the diastolic pressure, or deflated from a higher pressure in steps and held at each pressure step for duration more than one respiratory cycle. The control unit is connected to a pneumatic valve in such a way that the pneumatic valve is connected and placed between the pump and the cuff for controlling the inflation and deflation of the cuff while measuring the short-term variation in the systolic and diastolic blood pressures.

The cuff pressure is plotted against a measure of the pulse plethysmograph signal to obtain arterial pressure values. The empirical relationship between the cuff pressure and the pulse plethysmograph signal is determined using a parametric curve fit in order to yield a mean value curve and a variation curve providing a variation in pressure for each value of the plethysmograph signal. The mean value curve and the variation curve provide distribution of the systolic and diastolic pressure and an average pulse pressure.

The empirical relationship is determined by identifying a peak and trough in the plethysmograph waveform and plotting an area under a curve of each plethysmograph signal against the cuff pressure, where the area under each curve indicates a volume of blood in the finger with each pulse. The short term variation in the systolic and diastolic blood pressure is determined by tracing regression lines to depict a region with no experimentally-induced change in the blood flow and a region where the blood flow starts decreasing due to external pressure by the cuff, where an intersection of the two lines represents the diastolic pressure and a zero intercept represents the systolic pressure. The blood pressure variability is estimated as variation (eg. standard deviation) from the regression line after determining the systolic and diastolic pressure.

In another aspect of the present invention, a method for non-invasively measuring blood pressure variability includes a cuff that is wrapped around a limb of a subject and inflated using a pump pneumatically connected to the cuff. The photoplethysmogram sensor is placed and attached to a finger tip in the same limb of the subject distal to the cuff. A cuff pressure from the cuff and a pulse plethysmograph signal from the photoplethysmogram sensor is simultaneously acquired and recorded. An empirical relationship is derived between the cuff pressure and an amplitude measure of the plethysmograph signal in order to measure short-term variation in systolic and diastolic blood pressures at about the respiratory frequency.

The cuff is inflated from a low pressure below the diastolic pressure, or deflated from a higher pressure in steps and held at each pressure step for a duration more than a respiratory cycle. The empirical relationship is determined between the cuff pressure and the pulse plethysmograph signal using a parametric curve fit in order to yield a mean value curve and a variation curve providing a variation in pressure for each value of the plethysmograph signal The cuff pressure is plotted against a measure of the plethysmograph signal to obtain arterial pressure values. A peak and trough is identified in the plethysmograph signal and area under a curve of each plethysmograph signal is determined. An area under the curve of each pulse plethysmograph signal is plotted against the cuff pressure, where the area under each curve indicates a volume of blood in the finger with each pulse. A regression line is traced to depict a region with no experimentally-induced change in the blood flow and a region where the blood flow starts decreasing due to external pressure by the cuff, where an intersection of the two lines represents the diastolic pressure and a zero intercept represents the systolic pressure. The blood pressure variability is estimated as variation (eg. standard deviation) from the regression line after determining the systolic and diastolic pressure.

BRIEF DESCRIPTION OF THE DRAWINGS

The disclosed embodiments may be better understood by referring to the figures, in which reference numerals refer to identical or functionally-similar elements throughout the separate views, further illustrate the present invention and, together with the detailed description of the invention, serve to explain the principles of the present invention.

DETAILED DESCRIPTION OF THE INVENTION

The particular values and configurations discussed in these non-limiting examples can be varied and are cited merely to illustrate at least one embodiment and are not intended to limit the scope thereof.

In the following, numerous specific details are set forth to provide a thorough description of various embodiments. Certain embodiments may be practised without these specific details or with some variations in detail. In some instances, certain features are described in less detail so as not to obscure other aspects. The level of detail associated with each of the elements or features should not be construed to qualify the novelty or importance of one feature over the others.

The claimed subject matter has been provided here with reference to one or more features or embodiments. Those skilled in the art will recognize and appreciate that, despite the detailed nature of the exemplary embodiments provided here; changes and modifications may be applied to said embodiments without limiting or departing from the generally intended scope. These and various other adaptations and combinations of the embodiments provided here are within the scope of the disclosed subject matter as defined by the claims and their full set of equivalents. Like numbers refer to like elements throughout.

The present invention relates to an improved cost-effective non-invasive blood pressure monitoring system and method for estimating a range of systolic and diastolic pressures and their short-term variability. The non-invasive blood pressure measuring system uses a controlled pneumatic cuff, a respiration measurement device and a photoplethysmogram to enable estimation of the systolic and diastolic pressures during measurement of the blood pressure variability. The non-invasive blood pressure monitoring system is capable of accurately monitoring the range of blood pressure based on the cuff pressure, respiration cycles and photoplethysmography. The present invention is capable of accurately measuring an average systolic and diastolic pressure, mean pulse pressure and also their variability.

Figure 1:
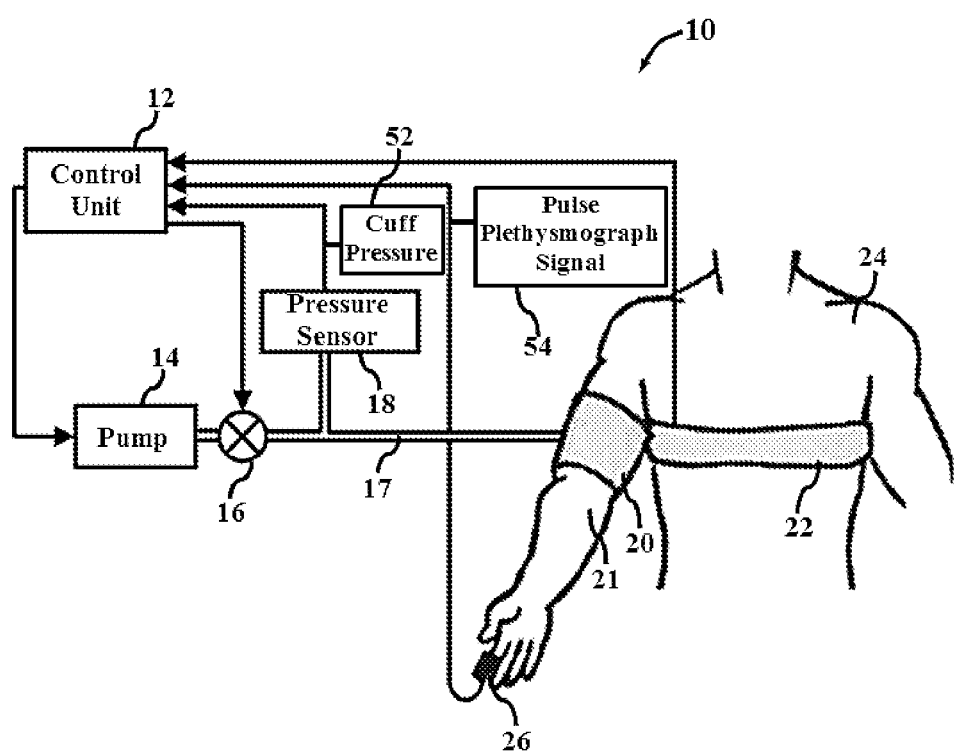
FIG. 1 illustrates a schematic arrangement of a non-invasive blood pressure measuring system, in accordance with the present invention.

FIG. 1 illustrates a schematic arrangement of a non-invasive blood pressure measuring system (10), in accordance with the present invention. In general, blood pressure variability is a better risk indicator than even absolute blood pressure values. The system (10) measures the short-term blood pressure variability (BPV) non-invasively. The system (10) measures distribution of systolic pressures, distribution of diastolic pressure and average pulse pressure in one or more full respiratory cycles, using a photoplethysmograph recording distal to a cuff inflated around a limb, and noting the changes in the plethysmogram with different cuff pressures.

Note that in FIGS. 1-11, identical or similar blocks are indicated by identical reference numerals. The blood pressure monitoring system (10) includes an inflatable cuff (20) wrapped around a limb (21) usually an upper arm of a subject (24), and the cuff (20) is wrapped snugly not tightly for blood pressure measurement. The cuff (20) is pneumatically connected to a pump (14) to inflate the cuff (20). A pneumatic valve (16) is connected to the pump (14) to control inflation and deflation of the cuff (20). The pneumatic pump (14) is capable of pumping up to 300 mmHg and the pneumatic valve (16) and pneumatic tubes (17) have a leak rate that is much smaller than the inflation rate of the pump (14).

The blood pressure measuring system (10) further includes a pressure sensor (18) associated with the cuff (20) for measuring cuff pressure (52). A photoplethysmogram sensor (26) is attached to a fingertip in the same limb (21) of the subject (24) and placed distal to the cuff (20) for monitoring blood flow and recording a pulse plethysmograph signal (54). In general, photoplethysmogram (PPG) is an optically obtained plethysmogram, a volumetric measurement of an organ. It is a low cost and non-invasive method that makes measurements at the surface of the skin and provides valuable information related to a cardiovascular system. Hereafter, the pulse plethysmograph signal (54) can also be referred as the pulse plethysmograph waveform (54) throughout the description only for the purpose of explanation but not by means of any limitations. The photoplethysmograph sensor (26) can be either reflective or transmittive photoplethysmograph and is placed at a point distal to the cuff (20) to provide a signal related to blood flow. Note that any other method of detecting blood flow distal to the cuff

(20) may also be used in lieu of photoplethysmograph sensor (26), depending upon design consideration.

Optionally, a respiration sensor (22) is placed on the chest of the subject (24) for monitoring respiratory movement. The respiration sensor (22) can be a chest distension sensor belt or a chest electrical impedance respiration sensor, based on design consideration. In a preferred embodiment, the cuff (20) is inflated from a low pressure well below diastolic pressure, for example, starting from 0 mmHg or deflated from a higher pressure in steps, such as 2 mmHg or more and held at each pressure step for duration not less than a respiratory cycle. The step size can be chosen to be large or small depending on the desired accuracy. A pressure step of 10 mmHg is suitable for standard measurement. It will be apparent, however, to those of skill in the art that such specifications and parameters can be altered without departing from the scope of the invention.

In a preferred embodiment, the maximum pressure of inflation can be less than the subject's (24) systolic pressure, can be about 80%. This pressure can be even less, if the subject (24) comfort requires it. At each pressure step, the pressure is held constant for a convenient duration involving a few respiratory cycles. The photoplethysmograph signal (54) from one or more complete respiratory cycles is taken for calculations. If the duration is less than or greater than multiples of full respiratory cycles, the measurement of short-term variability of blood pressure can be biased. While the cuff pressure (52) is held at each pressure step, the reading of the pulse photoplethysmogram sensor (26) is recorded.

The system (10) further includes a control unit (12) connected to the pressure sensor (18) and the photoplethysmogram sensor (26) for simultaneously recording the cuff pressure (52) and the plethysmograph signal (54). The control unit (12) derives an empirical relationship between the cuff pressure (52) and an amplitude measure of the plethysmograph signal (54) to measure the variation in the systolic and diastolic blood pressures. The cuff pressure (52) from the pressure sensor (18) and the continuous photoplethysmograph signal (54) from the photoplethysmogram sensor (26) are recorded simultaneously. Using a relationship between the two signals, average systolic, diastolic and pulse pressures and systolic and diastolic pressure variability occurring at about the respiratory frequency can be calculated.

Using the recorded pulse photoplethysmograph signal (54) and the cuff pressure (52), a relation between cuff pressure (52) and photoplethysmographically measured blood flow is determined using a parametric curve fit. In general, curve fitting is the process of constructing a curve, or mathematical function that has the best fit to a series of data points, possibly subject to constraints. Curve fitting can involve either interpolation, where an exact fit to the data is required, or smoothing, in which a "smooth" function is constructed that approximately fits the data.

This curve fitting yields a mean value curve and a variation curve, giving the variation in the pressure for each value of the plethysmographically estimated flow waveform (54). From these curves, the distributions of systolic and diastolic pressures, average pulse pressure and other parameters are obtained. The system (10) is based on obtaining the individualized empirical relationship of the amplitude measure of the photoplethysmogram signal (54) to the cuff pressure (52) and then deriving systolic and diastolic pressure.

Figure 2:
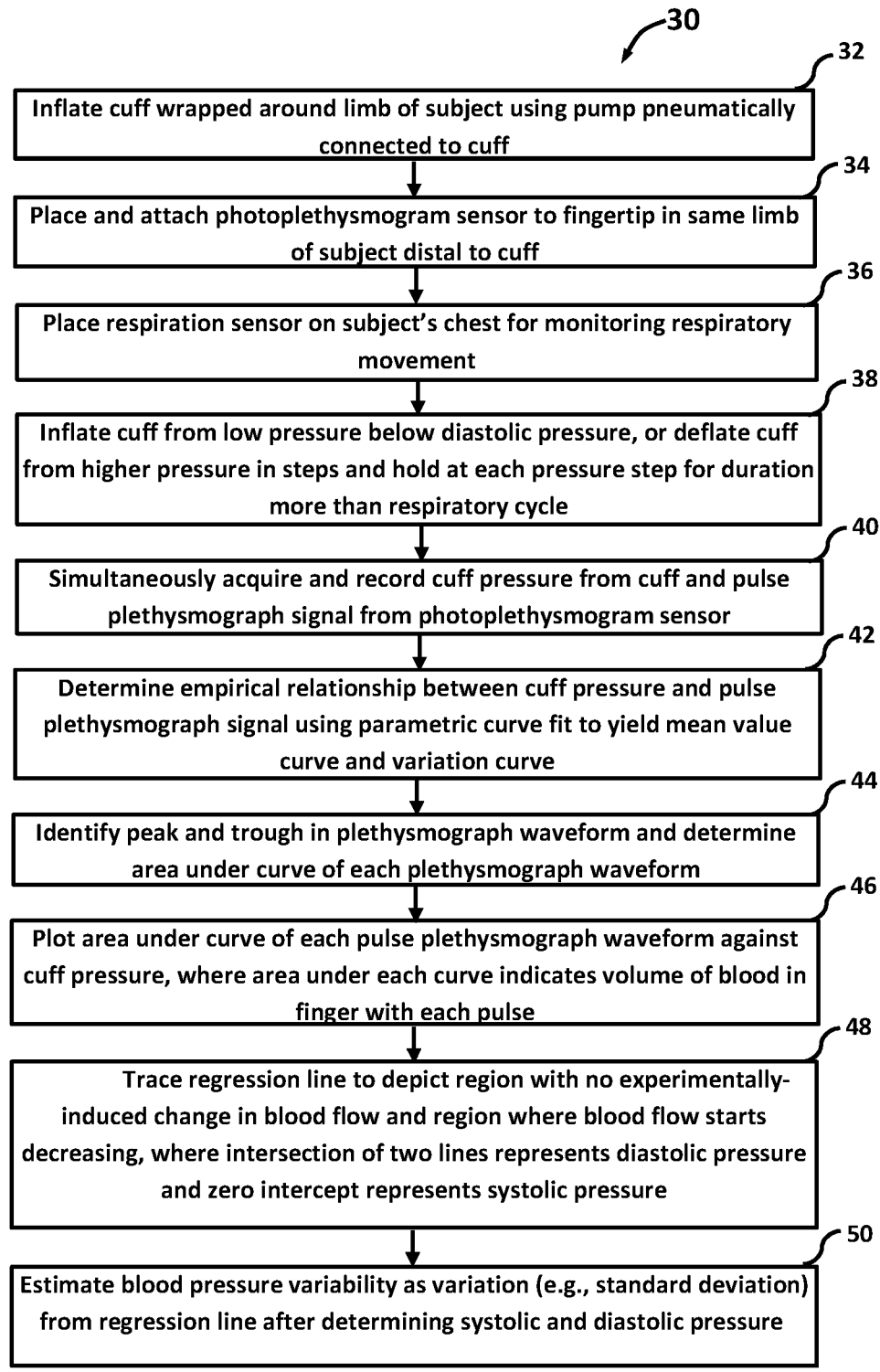
FIG. 2 illustrates a flowchart of operation illustrating a method for measuring a systolic and diastolic blood pressure and their beat-to-beat variability, in accordance with the present invention.

FIG. 2 illustrates a flowchart of operations illustrating a method (30) for measuring the systolic and diastolic blood pressure and their variability, in accordance with the present invention. Initially, the cuff (20) is wrapped around the limb (21) of the subject (24) and can be inflated or deflated using the pump (14) pneumatically connected to the cuff (20), as shown at block (32). The photoplethysmogram sensor (26) is placed and attached to the fingertip in the same limb (21) of the subject (24) distal to the cuff (20), as indicated at block (34). The respiration sensor (22) is placed on chest of the subject (24) to ensure measurement of the systolic and diastolic pressure variation for at least one respiratory cycle, as shown at block (36). The cuff (20) is inflated from low pressure below diastolic pressure, or deflated from higher pressure in steps and held at each pressure step for duration more than one respiratory cycle, as illustrated at block (38).

Figure 3:
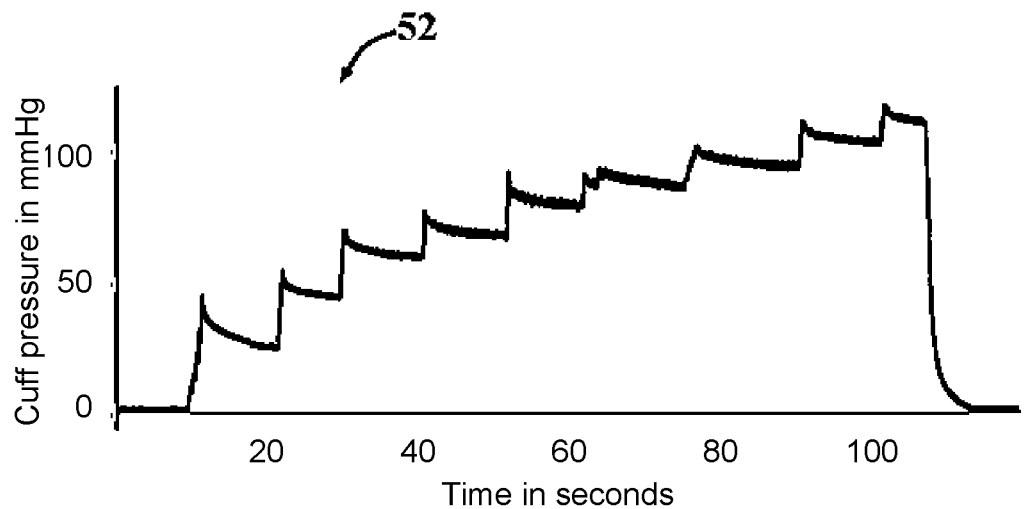
FIGS. 3-4 illustrate a graphical representation of a cuff pressure and a pulse plethysmograph signal, in accordance with the present invention.
Figure 4:
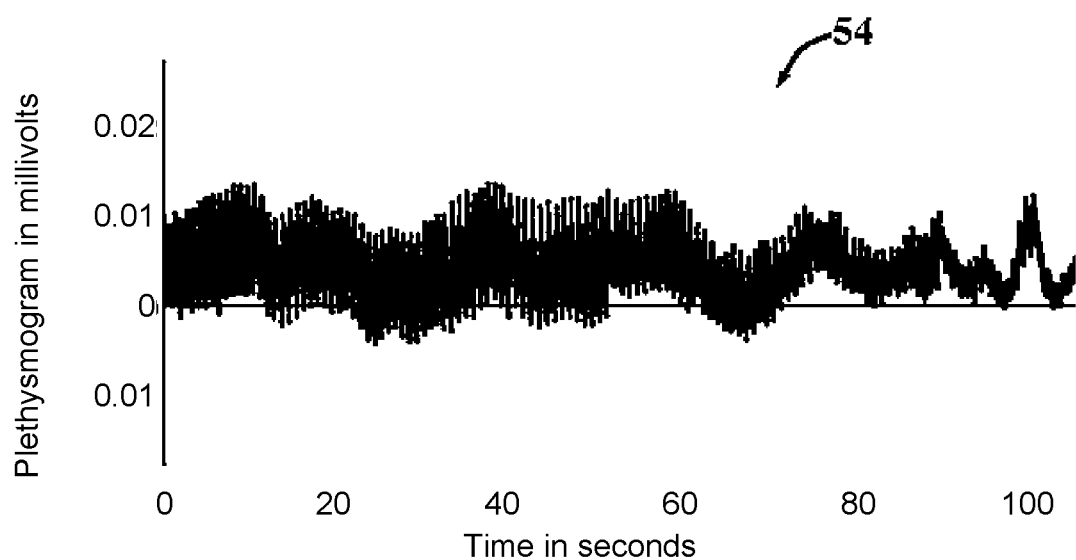

The cuff pressure (52) from the cuff (20) and the pulse plethysmograph signal (54) from the photoplethysmogram sensor (26) are simultaneously acquired and recorded, as indicated at block (40). Referring to FIGS. 3-4 a graphical representation of the cuff pressure (52) and the pulse plethysmograph signal (54) is illustrated, in accordance with the present invention. The cuff pressure (52) and the pulse plethysmograph signal (54) is acquired and digitized by the control unit (12) and stored on a computer. For example, the cuff (20) is inflated from 0 mmHg at 10 mmHg increments and held for 5 seconds at each level. The cuff pressure (52) is increased till the height of the plethysmograph (54) waves reduced to zero as shown in FIGS. 3-4.

Figure 5:
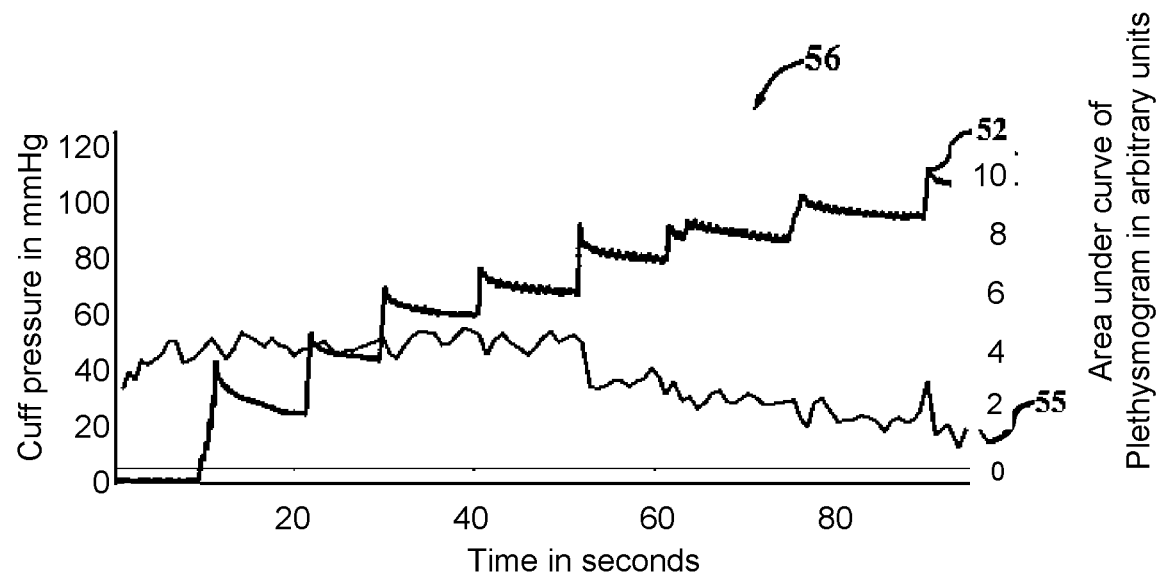
FIG. 5 illustrates a graphical representation of an overlay of area under curve of each pulse plethysmograph signal and the cuff pressure at similar time points, in accordance with the present invention.

An empirical relationship is derived between the cuff pressure (52) and an amplitude measure of the plethysmograph signal (54) to measure the variation of systolic and diastolic blood pressures at about the respiratory frequency as shown at block (42). Towards this, a peak and trough are identified in the plethysmograph waveform (54) and an area under a curve of each plethysmograph waveform (54) is determined, as indicated at block (44). Referring to FIG. 5 a graphical representation of an overlay (56) of area under curve (55) of each pulse plethysmograph waveform (54) and the cuff pressure (52) at the same time points is illustrated, in accordance with the present invention. The peaks and troughs in the plethysmograph signal (54) is identified and the area under curve (55) of each wave is calculated.

Figure 6:
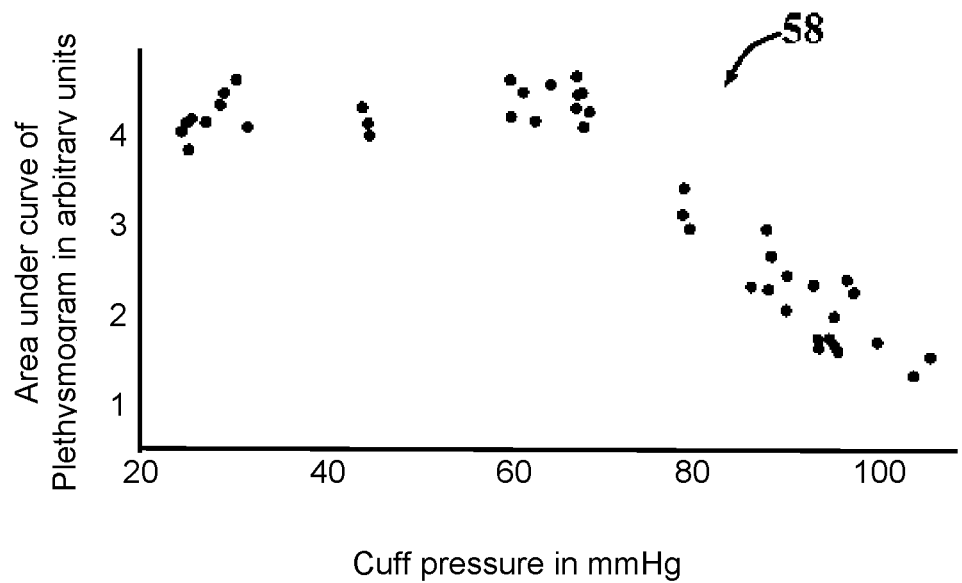
FIG. 6 illustrates a graphical representation of area under curve of each pulse plethysmograph signal plotted against the cuff pressure, in accordance with the present invention.

The area under the curve (55) of each pulse plethysmograph waveform (54) is plotted against the cuff pressure (52), where the area under each curve (55) indicates a volume of blood in the finger with each pulse, as shown at block (46). FIG. 6 illustrates a graphical representation (58) of the area under curve (55) of each pulse plethysmograph waveform (54) plotted against the cuff pressure (52), in accordance with the present invention.

Regression lines (62) and (64) are traced to depict a region with no experimentally-induced change in the blood flow and a region where the blood flow starts decreasing due to external pressure in the cuff, where an intersection (66) of the two lines (62) and (64) represents the diastolic pressure and a zero intercept (68) of the line (64) represents the systolic pressure, as indicated at block (48). The blood pressure variability is estimated as a variation (eg, standard deviation) from the intercepts (66) and (68) of the regression line (64) after determining the systolic and diastolic pressure, as shown at block (50).

Figure 7:
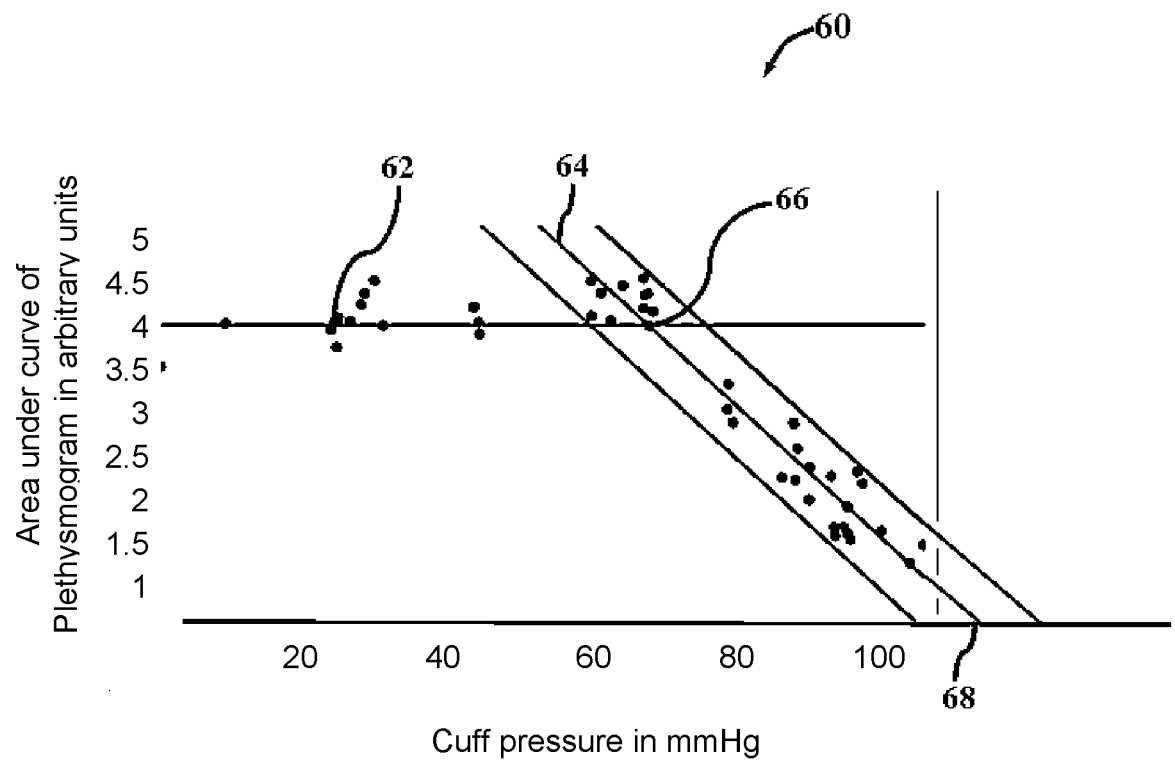
FIG. 7 illustrates a graphical representation of the area under curve of each pulse plethysmograph signal plotted against the cuff pressure with regression lines, in accordance with the present invention.

Referring to FIG. 7 a graphical representation 60 of the area under curve (55) of each pulse plethysmograph waveform (54) plotted against the cuff pressure (52) with regression lines (62) and (64) drawn to depict the regions with no experimentally-induced change in blood flow and the region where flow starts decreasing due to external pressure in the cuff is illustrated, in accordance with the present invention.

The area under curve (55) indicates volume of blood in the finger with each pulse. The point where the volume starts decreasing is when the cuff pressure (52) crosses (increases above) diastolic pressure. When the cuff pressure (52) crosses systolic pressure, there is no flow and the volume becomes zero. The regression lines (62) and (64) are drawn to depict the region with no experimentally-induced change in blood flow and the region where flow starts decreasing due to external pressure in the cuff respectively. The intersection (66) of the two lines (62) and (64) in the graph represents the diastolic pressure. Systolic pressure is the zero intercept (68) of the line (64). After estimation of the systolic and diastolic pressures, blood pressure variability is estimated as a variation (eg. Standard deviation) from the regression line (64).

Figure 8:
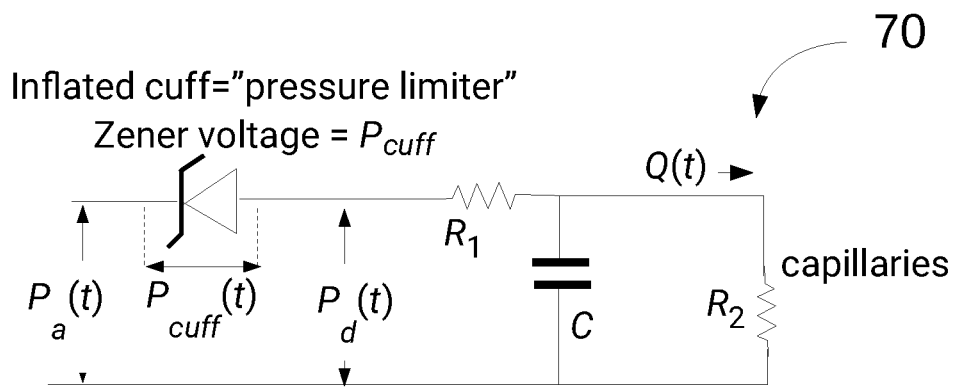
FIG. 8 illustrates an exemplary graphical representation of a resistive-compliant model of peripheral vasculature and an adjustable pressure cuff limiting arterial pressure distal to the cuff, in accordance with the present invention.

Referring to FIG. 8 an exemplary resistive-compliant model (70) of peripheral vasculature and the adjustable pressure cuff (20) limiting arterial pressure distal to the cuff (20) is illustrated, in accordance with the present invention. The following analysis obtains a relationship between the pulse plethysmographic waveform and the arterial pressure values. Because blood vessels are collapsible tubes, if vessel pressure is less than external pressure, the vessels are collapsed and no flow occurs. This property is represented by a Zener diode in the electrical equivalent. An adjustable pressure limiter is represented by an adjustable Zener diode (72) with breakdown voltage, $V_{zener}(t)$. This $V_{zener}(t)$ corresponds to the blood pressure cuff pressure, $P_{cuff}(t)$. In the experimental measurement the pressure cuff limits the arterial pressure distal to the cuff by $P_{cuff}$, if pressure proximal to cuff $>P_{cuff}$, and the blood flow is observed in the finger tip using the photoplethysmogram sensor (26). The arterial pressure proximal to the cuff $P_a(t)$ is analogous to the input voltage, and the finger blood flow, $Q(t)$, is analogous to the current through resistor $R_2$. The arterial pressure distal to the cuff is $P_d$ is represented as follows:

$$P_d(t) = \begin{cases} 0 \text{ for } P_a(t) \leq P_{cuff} \\ [P_a(t) - P_{cuff}] \text{ for } P_a(t) \geq P_{cuff} \end{cases} \quad (1)$$

The cuff pressure is increased in steps from a low pressure below the diastolic pressure to a maximum that is approximately equal to or higher than systolic pressure. From this model a relation between features of the measured flow waveform and features of arterial pressure waveform is derived as shown below in equation (2).

$$P_d(t) = R_1 C \frac{d}{dt} V_o(t) + \left(1 + \frac{R_1}{R_2}\right) V_o(t) \quad (2)$$

$$Q(t) = \frac{P_o(t)}{R_2}$$

Equations (1) and (2) define the blood flow in the finger as seen in a photoplethysmogram sensor (26). Note that equation (1) is a non-linear function. $P_d(t)$ is non-zero only when the arterial pressure exceeds the cuff pressure as given by equation (1). Taking the Fourier transform and rearranging equation (2) the flow is represented in terms of simple algebraic operations:

$$Q(j\omega) = \frac{P_d(j\omega)}{Z(j\omega)} \text{ where } Z(j\omega) = \frac{1}{R_1 + R_2 + j\omega R_1 R_2 C} \quad (3)$$

Figure 11:
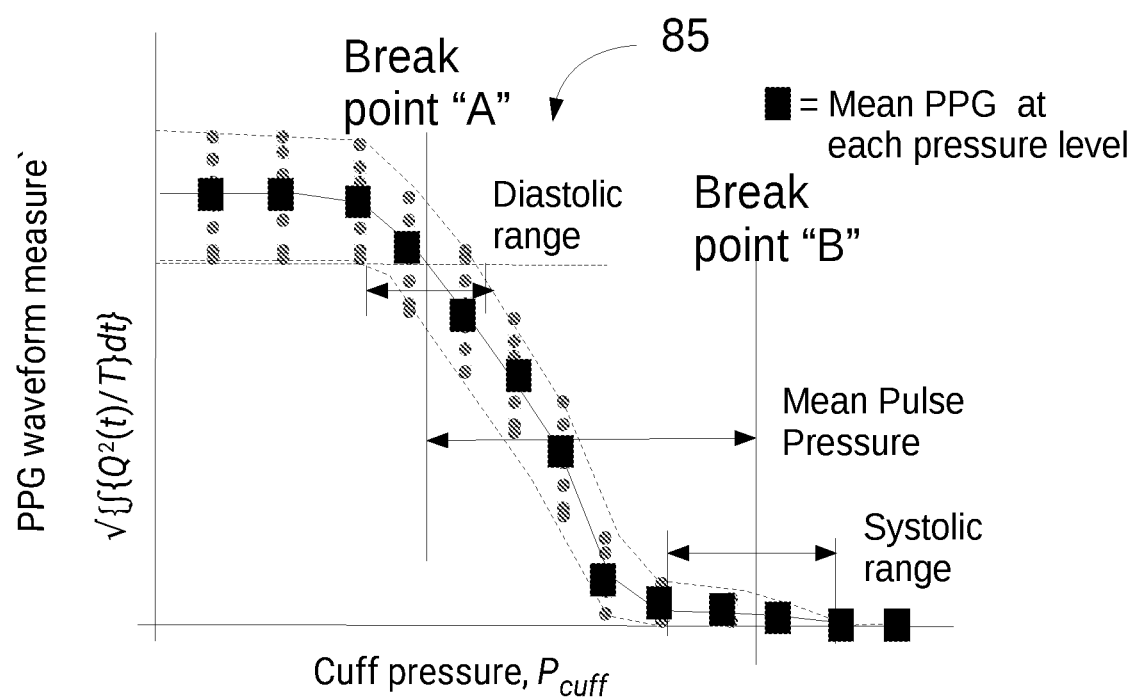

This gives the relation between the measured flow and the cuff and arterial pressures in the Fourier or frequency domain. The flow waveform varies with cuff pressure (52) when (a) the cuff pressure (52) is greater than the minimum arterial pressure (diastolic pressure) and (b) the maximum arterial pressure is greater than the cuff pressure (52). These two points are of interest, and are called breakpoint 'A' and breakpoint 'B' as shown in FIG. 11. These breakpoints are well defined and represent physiologically meaningful points. In order to do calculations in the time domain, the root of the square of equation (3) is determined as follows:

$$\sqrt{\int |Q(j\omega)|^2 d\omega} = \sqrt{\int \frac{|P_d(j\omega)|^2}{|Z(j\omega)|^2} d\omega} \quad (4)$$

Using Parseval's theorem the quantity on the LHS can be calculated from the time waveform:

$$\int |Q(j\omega)|^2 d\omega = \frac{1}{T} \int |Q(t)|^2 dt \quad (5)$$

where T is the period of the cardiac cycle waveform. Equation (4) shows that the RMS value of the time waveform from the plethysmogram relate the flow and the cuff pressure (52). Using equations (1, 3, 5) the RMS value of the flow waveform is zero when $P_{cuff} > P_a$ and maximum when $P_{cuff} \ll P_a$. For intermediate values of $P_{cuff}$, the RMS value of the flow waveform is in-between. The exact relation between the RMS value of flow and the arterial pressure vary with individuals and settings. Therefore, in general, only empirical relations are available. Although the RMS value of flow is used in this discussion based on a simple impedance model of the vasculature, other measures like area under the curve or peak-to-peak amplitude may be used.

The right hand side of equation (4) involves the ratio of the pressure to the impedance. Therefore, the relation between measured flow and pressure is not simply proportional. In a very simple case where the impedance $Z(j\omega)$ is a simple constant, the pressure can be estimated accurately from the flow using equation (3), by a simple constant of proportionality. But this is not usually tenable. In general, the impedance $Z(j\omega)$ is a complex function and the relationship between flow and pressure will depend on the wave shape.

Figure 9:
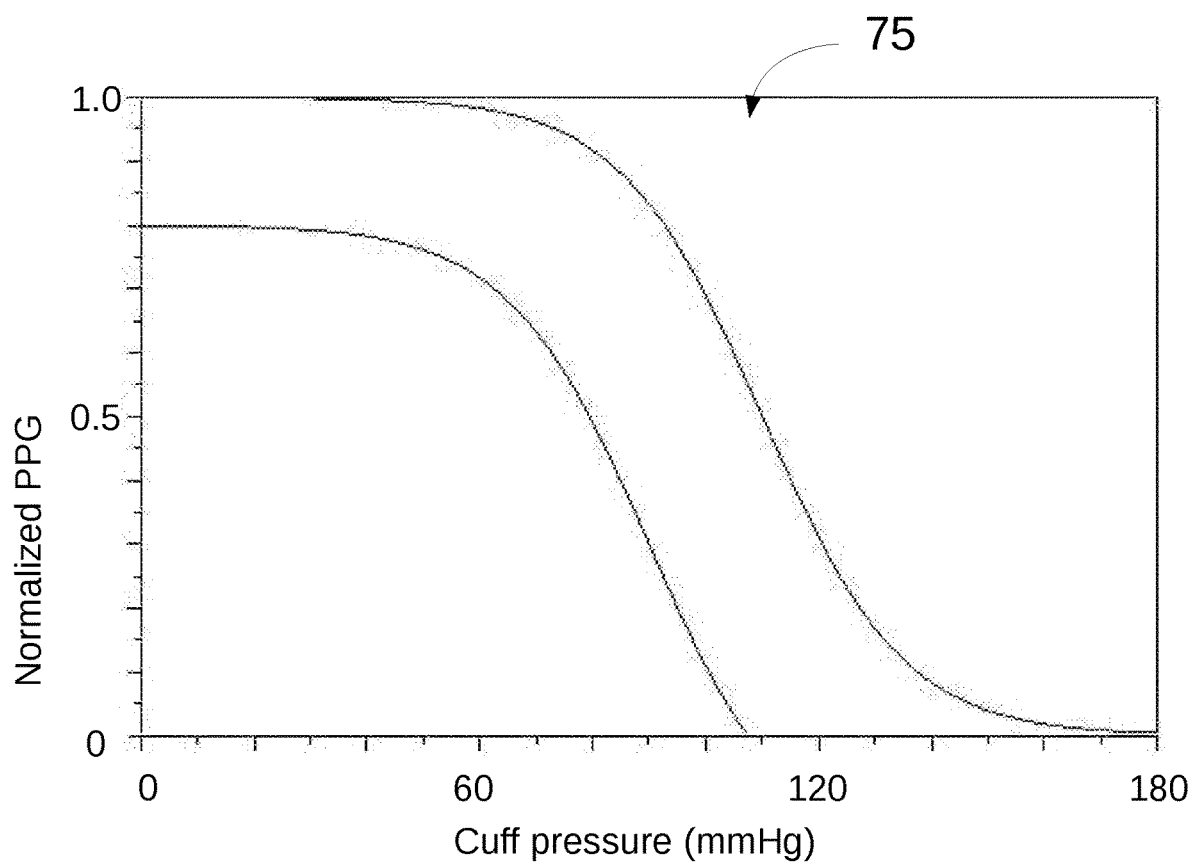
FIG. 9 illustrates an exemplary graphical representation with pressure on a horizontal axis (mmHg) and a normalized feature of flow on a vertical axis, in accordance with the present invention.

In an individual in a short interval of time, the impedance $Z(j\omega)$ may be assumed to be unchanging, although it is a complex function of frequency. The relationship between pressure and flow in such a situation may be assumed to be unchanging. From equation (1), if $P_{cuff}$ is adjusted carefully, so that the measure of $Q(t)$ is zero, then $P_{cuff} = P_a$, and can be used to determine the value of systolic pressure. This method can also be used to determine the variation in systolic pressure. This can be an exact measure. Using equation (1), if $P_{cuff}$ is titrated so that the measure of $Q(t)$ is exactly the same as when $P_{cuff}$ is zero, then the diastolic pressure and its variation can be determined. This however, cannot be an exact measure as small variations of waveform shape and size are inevitable in normal conditions. Plotting the cuff pressure (52) against a measure of the photoplethysmograph waveform, the arterial pressure values can be obtained. With increasing cuff pressure (52), the residual flow as measured by the plethysmogram follows a logistic function (i.e., a quenching function) which can be described algebraically by a function of the form:

$$\text{Flow}(P) = 1 - \frac{1}{1 + e^{-K(P-M)}} \tag{6}$$

where 'P' represents the cuff pressure (52) and the plethysmographic flow ('Flow') is dependent on the cuff pressure (52). 'M' is the mean value of the flow waveform, IC is steepness of curve. FIG. 9 illustrates a graphical representation (75) of a logistic function plotted for the pressure on the horizontal axis (mmHg) and a normalized feature of flow on the vertical axis, in accordance with the present invention. The two curves are the boundaries of the variation in blood pressure.

Figure 10:
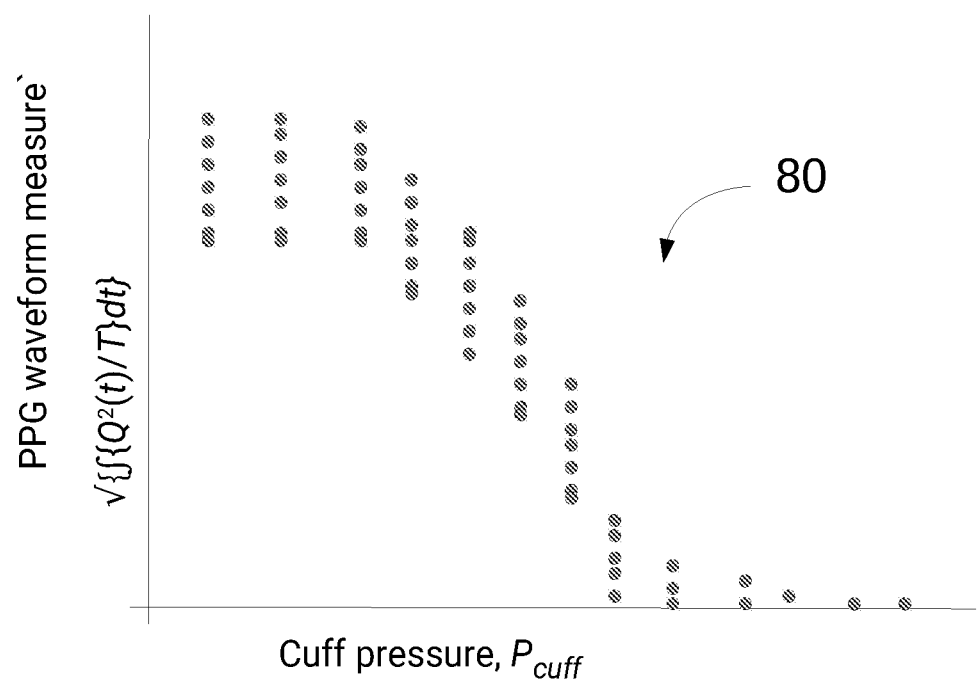
FIGS. 10-11 illustrates an exemplary graphical representation of the pulse plethysmograph signal at each pressure level for estimating the systolic and diastolic blood pressure and their short-term variability, in accordance with the present invention.

FIGS. 10-11 illustrate an exemplary graphical representation (80 and 85) of an amplitude measure of the pulse plethysmograph signal (54) at each pressure level, in accordance with the present invention. The mean value of the amplitude measure of the pulse plethysmograph signal (54) at each pressure level is calculated. Three curves can be fit to the data, (a) the maximum pulse plethysmograph signal value at each pressure, (b) minimum pulse plethysmograph signal value at each pressure and (c) mean pulse plethysmograph signal value at each pressure, as shown in FIG. 11.

From the maximum pulse plethysmograph signal value at each pressure and minimum pulse plethysmograph signal value at each pressure, the range of diastolic can be estimated as the intersection of these curves with a horizontal line extended from the minimum pulse plethysmograph signal value at zero cuff pressure, and the range of systolic pressures can be estimated as the intersection of these curves with the X-axis (pressure axis), as shown in FIG. 11. The intersection of the mean value curve with the two horizontal lines gives the estimate of the mean pulse pressure.

The choice of curve to fit the data determines the accuracy of estimation of the values. Fine-tuning and validation of the system (10) by comparison against an intra-arterial recording may establish the system (10) as the most preferred for measuring blood pressure, as the system (10) gives more accurate estimates of blood pressure than existing systems, and the system (10) also assesses blood pressure variations at about the respiratory frequency (short-term blood pressure variability). The present system (10) assesses the short-term blood pressure variability non-invasively, and with community level studies, the system (10) will replace the conventional methods which are inaccurate.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

We claim:

1. A non-invasive blood pressure variability measuring system (10), comprising: a cuff (20) pneumatically connected to a pump (14) to inflate the cuff (20) to be wrapped around a limb (21) of a subject (24);
a pressure sensor (18) associated with the cuff (20) for measuring a cuff pressure (52);
a photoplethysmogram sensor (26) attached to a fingertip in the same limb (21) of the subject (24) and placed to be distal to the cuff (20) for monitoring blood flow and recording a pulse plethysmograph signal (54); and
a control unit (12) connected to the pressure sensor (18) and the photoplethysmogram sensor (26),
the system (10) configured to measure a variation in systolic and diastolic blood pressures at a frequency corresponding to that of a respiratory cycle of the subject,
wherein the system is configured to either inflate the cuff (20) from a low pressure below the diastolic pressure or deflate the cuff from a pressure higher than the systolic pressure, in steps and hold the pressure at a constant level at every step for a duration of more than one respiratory cycle of the subject,
the control unit (12) configured to simultaneously record the cuff pressure (52) and the plethysmograph signal (54) such that an empirical relationship is derived between the cuff pressure (52) and an amplitude measure of the plethysmograph signal (54), and at the same time to assess a distribution of systolic and diastolic pressures, by obtaining variations in the plethysmograph signal during every pressure step,
wherein the empirical relationship between the cuff pressure (52) and the amplitude measure of the pulse plethysmograph signal (54) is nonlinear and is determined using a parametric curve fit, and the system is configured to yield a mean value curve and variation curves (85) providing a variation in pressure for each value of the pulse plethysmograph signal (54), wherein the mean value curve and the variation curves provide the distribution of the systolic and diastolic pressures,
wherein the empirical relationship between cuff pressure and pulse plethysmograph signal is determined by identifying a peak and trough in the pulse plethysmograph signal (54) and plotting an area under the curve (55) of each pulse plethysmograph signal (54) against the cuff pressure (52), wherein the area under each curve (55) indicates a volume of blood in the finger with each pulse, to yield the range of systolic and diastolic pressures.

2. The system of claim 1, wherein the respiration sensor (22) includes a chest distension sensor belt or a chest electrical impedance respiration sensor and wherein the photoplethysmogram sensor (26) includes a reflective plethysmograph sensor or a transmittive plethysmograph sensor.

3. The system of claim 1, wherein the system is configured to deflate the cuff from a pressure higher than the systolic pressure in steps and hold the pressure at a constant level at each of the steps for the duration of more than the one respiratory cycle.

4. The system of claim 1, wherein the control unit (12) is connected to a pneumatic valve (16) in such a way that the pneumatic valve (16) is connected and placed between the pump (14) and the cuff (20), the control unit (12) configured to control the inflation and deflation of the cuff (20), the system (10) configured to measure the short term variation in the systolic and diastolic blood pressure.

5. The system of claim 1, wherein the cuff pressure (52) is plotted against an amplitude measure of the pulse plethysmograph signal (54) to obtain the range of systolic and diastolic pressures.

6. The system of claim 1, wherein the range of systolic and diastolic blood pressures are determined by tracing two regression lines (62, 64), and the first line (62) to depict a region with no experimentally-induced change in the blood flow and the second line (64) to depict a region where the blood flow starts decreasing due to an external cuff pressure, wherein an intersection (66) of the two lines (62, 64) represents the average diastolic pressure and a zero intercept (68) of the line (64) represents the average systolic pressure, and the intersections of the variation curves with a horizontal line extended from the minimum pulse plethysmograph signal value at zero cuff pressure represents the diastolic pressure range (85) and zero intercepts of the variation curves represents the systolic pressure range.

7. A method (30) for non-invasively measuring blood pressure variability, comprising: inflating a cuff (20) wrapped around a limb (21) of a subject (24) using a pump (14) pneumatically connected to the cuff (20);
   placing and attaching a photoplethysmogram sensor (26) to a fingertip in the same limb (21) of the subject (24) distal to the cuff (20);
   simultaneously acquiring and recording a cuff pressure (52) from the cuff (20) and a pulse plethysmograph signal (54) from the photoplethysmogram sensor (26); and
   including either inflating the cuff (20) from a low blood pressure below the diastolic blood pressure, or deflating the cuff from a pressure higher than the systolic pressure, in steps and holding the pressure at a constant level at each of the steps for a duration more than one respiratory cycle of the subject;
   deriving an empirical relationship between the cuff pressure (52) and an amplitude measure of the plethysmograph signal (54), and at the same time to assess a distribution of systolic and diastolic pressures by obtaining variations in the plethysmograph signal during every pressure step, and thereby measuring a variation in systolic and diastolic blood pressures at a frequency corresponding to that of a respiratory cycle of the subject,
   determining the empirical relationship between the cuff pressure (52) and the amplitude measure of the pulse plethysmograph signal (54) using a parametric curve fit in order to yield a mean value curve and variation curves (85) providing variations in systolic and diastolic pressures for each value of the pulse plethysmograph signal (54);
   identifying a peak and trough in the pulse plethysmograph signal (54) and determining an area under a curve (55) of each pulse plethysmograph signal (54);
   plotting an area under the curve (55) of each pulse plethysmograph signal (54) against the cuff pressure (52), where the area under each curve (55) indicates a volume of blood in the finger with each pulse; and
   tracing two regression lines (62, 64) to the mean value curve, the first line (62) to depict a region with no experimentally-induced change in the blood flow and the second line (64) to depict a region where the blood flow starts decreasing due to an external cuff pressure, wherein an intersection (66) of the two lines (62, 64) represents the average diastolic pressure and a zero intercept (68) of the line (64) represents the average systolic pressure, and the intersections of the variation curves with a horizontal line extended from the minimum pulse plethysmograph signal value at zero cuff pressure represents the diastolic pressure range (85) and zero intercepts of the variation curves represents the systolic pressure range.

8. The method of claim 7, further comprising plotting the cuff pressure (52) against a measure of the pulse plethysmograph signal (54) to obtain the variation in systolic and diastolic pressures.

* * * * *